(12) United States Patent
Samuel

(10) Patent No.: US 6,792,662 B2
(45) Date of Patent: Sep. 21, 2004

(54) NEEDLE PULLER FOR DESTROYING HYPODERMIC NEEDLES

(75) Inventor: P. R. Suresh Samuel, Coimbatore (IN)

(73) Assignee: Becton Dickinson and Company, Franklin Lakes, NJ (US)

( * ) Notice: Subject to any disclaimer, the term of this patent is extended or adjusted under 35 U.S.C. 154(b) by 58 days.

(21) Appl. No.: 10/074,312

(22) Filed: Feb. 12, 2002

(65) Prior Publication Data

US 2003/0029014 A1 Feb. 13, 2003

Related U.S. Application Data

(60) Provisional application No. 60/311,692, filed on Aug. 10, 2001.

(51) Int. Cl.[7] .............................................. B23P 19/00
(52) U.S. Cl. ........................ 29/426.5; 29/240; 29/456; 29/244; 604/110; 206/366
(58) Field of Search ................... 29/426.1, 426.4, 29/426.5, 777, 240, 244, 267, 456; 206/365, 366; 604/110; 83/167, 944

(56) References Cited

U.S. PATENT DOCUMENTS

| | | | |
|---|---|---|---|
| 3,404,593 A | 10/1968 | Arcarese et al. | 83/167 |
| 3,469,750 A | 9/1969 | Vanderbeck | 225/94 |
| 3,686,733 A | 8/1972 | Johan et al. | 83/199 |
| 3,785,233 A | 1/1974 | Robinson | 83/167 |
| 3,851,555 A * | 12/1974 | Eldridge et al. | 83/167 |
| 3,914,865 A | 10/1975 | Oakes | 30/131 |
| 4,035,911 A | 7/1977 | Nethercutt et al. | 30/131 |
| 4,255,996 A | 3/1981 | Choksi et al. | 83/140 |
| 4,275,628 A | 6/1981 | Greenhouse | 83/167 |
| 4,315,448 A | 2/1982 | Ball | 83/167 |
| 4,375,849 A | 3/1983 | Hanifl | 206/366 |
| 4,531,437 A * | 7/1985 | Szablak et al. | 83/167 |
| 4,614,035 A | 9/1986 | Andrews | 30/124 |
| 4,807,344 A * | 2/1989 | Kelson et al. | 29/240 |
| 4,956,907 A * | 9/1990 | Bruno | 29/426.5 |
| 4,986,811 A * | 1/1991 | Thead et al. | 604/110 |
| 4,989,307 A * | 2/1991 | Sharpe et al. | 29/240 |
| 5,067,223 A * | 11/1991 | Bruno | 29/426.5 |
| 5,091,621 A | 2/1992 | Butler | 219/68 |
| 5,187,850 A * | 2/1993 | McCammon et al. | 206/366 |
| 5,312,346 A * | 5/1994 | Han | 604/110 |
| 5,351,381 A * | 10/1994 | Case | 29/426.4 |
| 5,573,113 A | 11/1996 | Shillington et al. | 206/366 |
| 5,736,706 A | 4/1998 | Butler | 219/68 |
| 5,933,936 A * | 8/1999 | Wand | 29/240 |
| 5,947,950 A * | 9/1999 | Shillington et al. | 206/366 |
| 6,158,314 A | 12/2000 | Thead et al. | 83/23 |

* cited by examiner

*Primary Examiner*—David P. Bryant
(74) *Attorney, Agent, or Firm*—Jeanne P. Lukasavage; John L. Voellmicke

(57) ABSTRACT

A needle removal/destruction apparatus for pulling a metal needle free from a plastic hypodermic syringe, while also deforming the metal needle to prevent reuse thereof. The apparatus includes a container having a rotatable needle removing fixture mounted therein. A metal needle hypodermic syringe is inserted within the rotatable needle removing fixture, which is thereafter rotated to pull the needle free of the needle hub while also permanently deforming the needle to prevent subsequent reuse thereof.

19 Claims, 16 Drawing Sheets

NEEDLE PULLER FOR DESTROYING HYPODERMIC NEEDLES

This application claims the benefit of U.S. Provisional Application No. 60/311,692 filed Aug. 10, 2001.

BACKGROUND OF THE INVENTION

The present invention relates to a needle puller and, more particularly, to an apparatus which both removes a needle from a syringe and also deforms the needle to prevent reuse thereof.

In today's medical profession, most injections are given with disposable hypodermic syringes, which are supplied to hospitals and doctors offices in sterile packages. To ensure sterility and to prevent any accidental contamination between patients, the hypodermic syringe is discarded after a single use. It will be appreciated that due to the size of the medical establishment, a great number of syringes are used and disposed of on a daily basis.

A significant amount of energy has been devoted to the issue of safely disposing of used syringes. Although various methods/apparatuses exist for disposing of the entire used syringe, there are disadvantages associated with the disposal of the entire used syringe. In particular, the disposal of the entire used syringe does not prevent a subsequent handler of the syringe from suffering a needlestick injury, nor does it prevent the used syringe from being reclaimed for use with illegal drugs.

The prior art, which is replete with patents directed to needle destroying apparatuses, can be generally divided into two categories: 1) those devices which involve the destruction of the needle by shearing at least a portion of the needle from the used syringe, and 2) those devices involving the destruction of the needle through the electrical melting of such needle.

The prior art devices relating to shearing involve the cutting of the metal needle to remove the sharpened point (which also prevents subsequent reuse of such needle) or the cutting of the syringe (which destroys the syringe thus preventing reuse of such syringe). Although cutting of the needle prevents the subsequent reuse of such needle, this technique has several significant disadvantages, namely: 1) that the shearing blade becomes dull after repeated uses, thereby limiting the life of the device, 2) the sheared needle hub typically exhibits sharp edges which may still result in subsequent needlestick injuries, and 3) at least a portion of the destroyed syringe includes both metal and plastic thereby increasing the difficulty of subsequent disposal and/or recycling.

The second category of prior art devices involve the electrical melting of at least a portion of the metal needle. Although melting of a portion of the needle prevents subsequent reuse of the syringe, such devices still suffer from several significant disadvantages, including: 1) the requirement of a power source, which typically adds bulk and expense to the apparatus, and limits the location of such apparatus, 2) the inability to ensure complete segregation of materials, that is, separation of the metal and plastic components of the syringe, and 3) the inability to ensure that sharpened edges do not remain on the destroyed syringe.

There is therefore a need in the prior art for a device which satisfactorily destroys a hypodermic syringe without the necessity of shearing (eliminating sharp edges which can result in subsequent needlestick injury and the need for blade(s) which must be regularly sharpened/replaced), which does not require a heating source and/or electrical power, and which results in complete segregation of the different materials of the syringe to facilitate subsequent disposal and/or recycling of the used syringe.

SUMMARY OF THE INVENTION

The present invention, which addresses the needs of the prior art, provides an apparatus for removing a needle from a medical device. The apparatus includes a container defining a chamber. The container includes a container top having an aperture communicating with the chamber. The apparatus further includes a needle removing fixture mounted to the container and rotatable with respect thereto free of shearing surfaces. The needle removing fixture is positioned at least partially within the chamber and includes a passage for receiving a needle extending through the aperture in the container top. Finally, the apparatus includes means for rotating the needle removing fixture.

The present invention further provides an apparatus for removing a needle from a medical device. The apparatus includes means for maintaining the medical device in a substantially stationary position. The apparatus further includes means for retaining a needle attached to a medical device. Finally, the apparatus includes means for rotating the retaining means about a generally horizontal axis free of shearing surfaces.

The present invention is also directed to a method of removing a needle from a medical device. The method includes the step of inserting the needle of the medical device into a passage of a needle removing fixture. The method includes the further step of rotating the needle removing fixture about an axis while maintaining the medical device in a substantially stationary position thereby removing the needle from the medical device without shearing thereof.

The present invention further relates to a method of removing a metal needle from a plastic hub of a medical device. The method includes the step of securing the medical device in a substantially stationary position whereby the needle is located at a predetermined position. The method includes the further step of disconnecting the metal needle from the plastic hub without shearing of the needle while simultaneously deforming the metal needle to prevent reuse thereof.

Finally, the present invention relates to an apparatus for removing a needle from a medical device. The apparatus includes a container defining a chamber. The container includes a container top having a first aperture communicating with the chamber. The apparatus further includes a recessed sleeve extending from the container top into the chamber. The container top includes a second aperture communicating with the sleeve. The second aperture has a diameter greater than the diameter of the first aperture. The sleeve includes a third aperture communicating with the chamber. The third aperture is substantially coaxially aligned with the second aperture. The apparatus also includes a needle removing fixture mounted to the container and rotatable with respect thereto free of sheering surfaces. The needle removing fixture is positioned at least partially within the chamber and includes first and second working sections having diameters $D_1$ and $D_2$, respectively, wherein $D_1$ is greater than $D_2$. The first working section includes a first passage for receiving a needle extending through the first aperture in the container top. The second working section includes a second passage for receiving a needle extending through the third aperture and the recessed sleeve. Finally, the apparatus includes means for rotating the needle-removing fixture.

As a result, the present invention provides an apparatus (and accompanying method) for safely and permanently disposing of used hypodermic syringes. First, because the needle is removed from the barrel of the syringe, subsequent needlestick injuries during handling of the used syringe are avoided. Needlestick injuries are further avoided because the entire needle is pulled from the needle hub without leaving any sharp metal stubs which would otherwise remain if such needle was removed by shearing, rather than being pulled out of the hub. Second, the needle itself is permanently deformed during the disassembly process, thereby preventing any attempt to subsequently reuse the needle. Third, the apparatus of the present invention (by completely separating the metal needle from the plastic hub and barrel) results in complete segregation of the plastic and metal components of a hypodermic syringe, thus facilitating subsequent disposal and/or recycling of the materials. Fourth, the apparatus of the present invention exhibits a long field life in that there are no parts subject to wear, such as shearing blades used in certain prior art devices. Fifth, the apparatus of the present invention does not require any external source of power, thereby facilitating its use in the field.

DETAILED DESCRIPTION OF THE INVENTION

Figure 1:
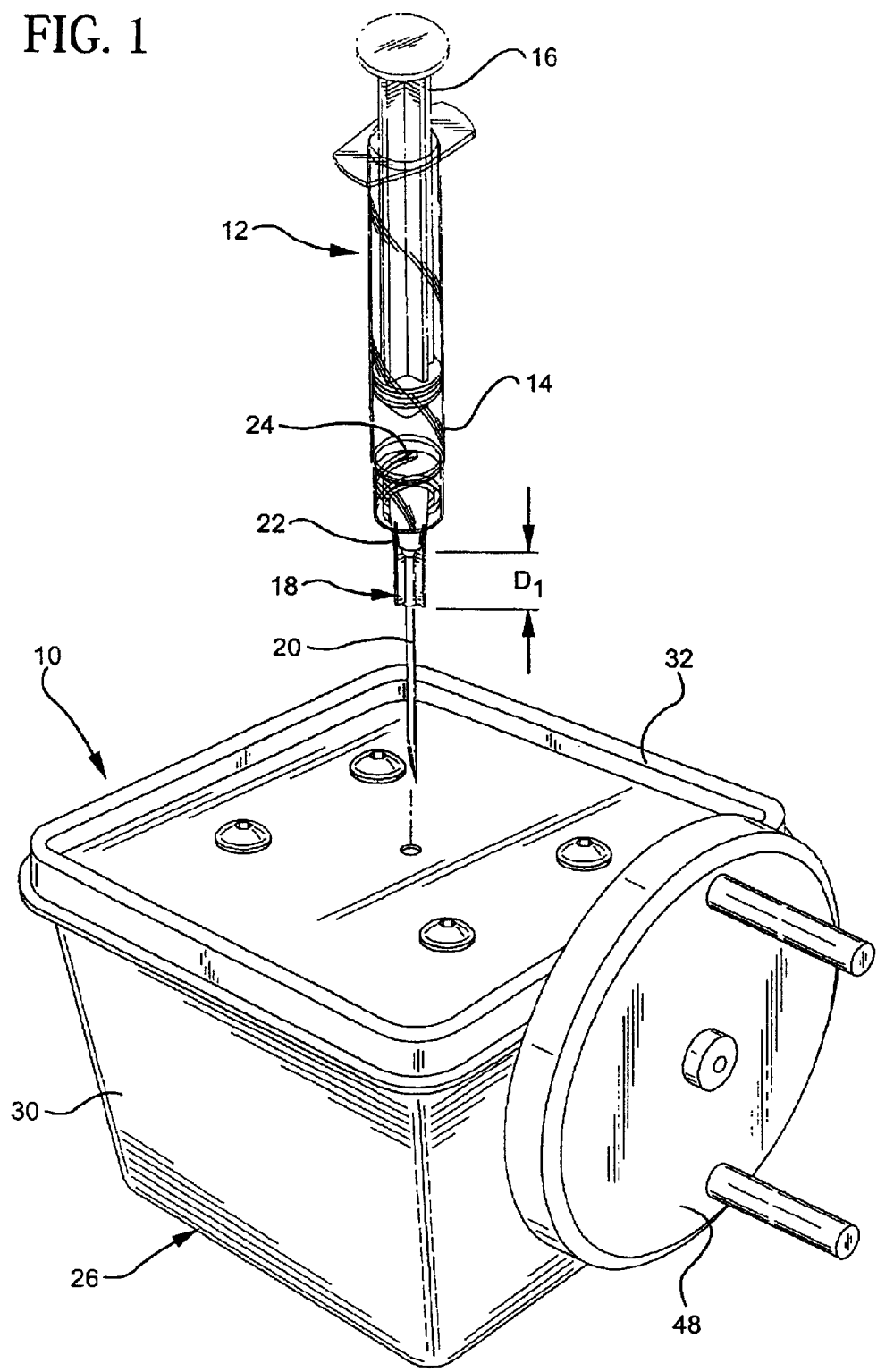
FIG. 1 is a perspective view showing the needle removal/destruction apparatus of the present invention with a hypodermic syringe positioned thereabove.

Referring to the drawings, and in particular to FIG. 1, a needle removal/destruction apparatus 10 in accordance with the present invention is shown. As will be described more fully hereinbelow, apparatus 10 is used by medical personnel to safely and permanently dispose of a used hypodermic syringe 12.

As will be understood by those skilled in the art, hypodermic syringe 12 typically includes a plastic barrel 14, a plastic plunger 16 cooperating with the mentioned barrel, and a needle assembly 18. Needle assembly 18 includes a sharpened metal cannula, i.e., needle 20, which is supported at its non-sharpened end by a plastic needle hub 22. Needle 20 extends into hub 22 a distance $D_1$, which defines a glue well for bonding the needle to the hub. The length of this glue well varies for different sized needles, but is typically on the order of approximately 8 mm. A twist-lock connection 24 allows needle assembly 18 to be secured to barrel 14. Needle 20 may of course be secured to the barrel of the syringe in other known fashions, e.g., needle 20 may be directly secured to a needle hub integrally formed with barrel 14.

Figure 2:
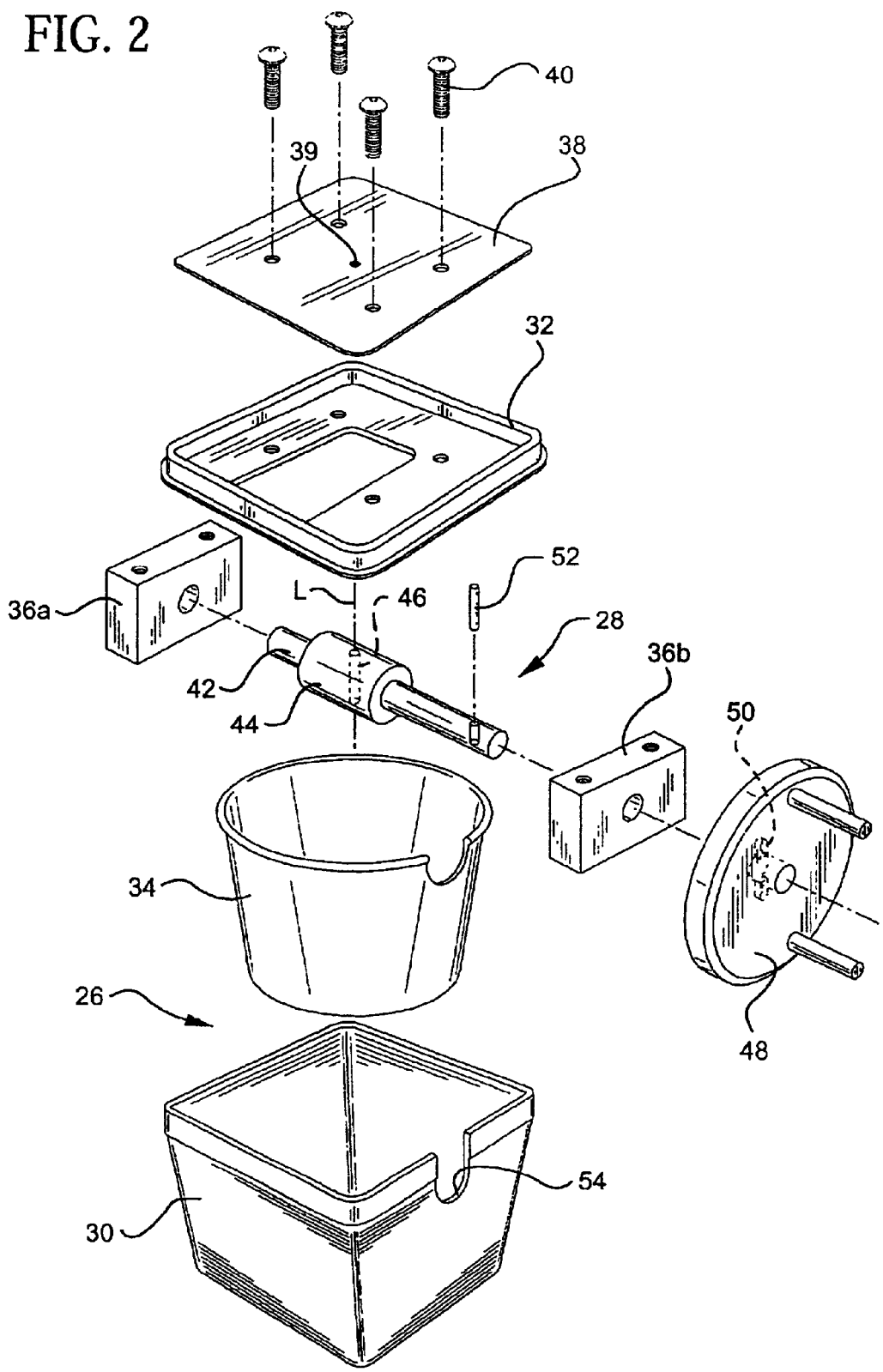
FIG. 2 is an exploded perspective view of the needle removal/destruction apparatus of FIG. 1.
Figure 3:
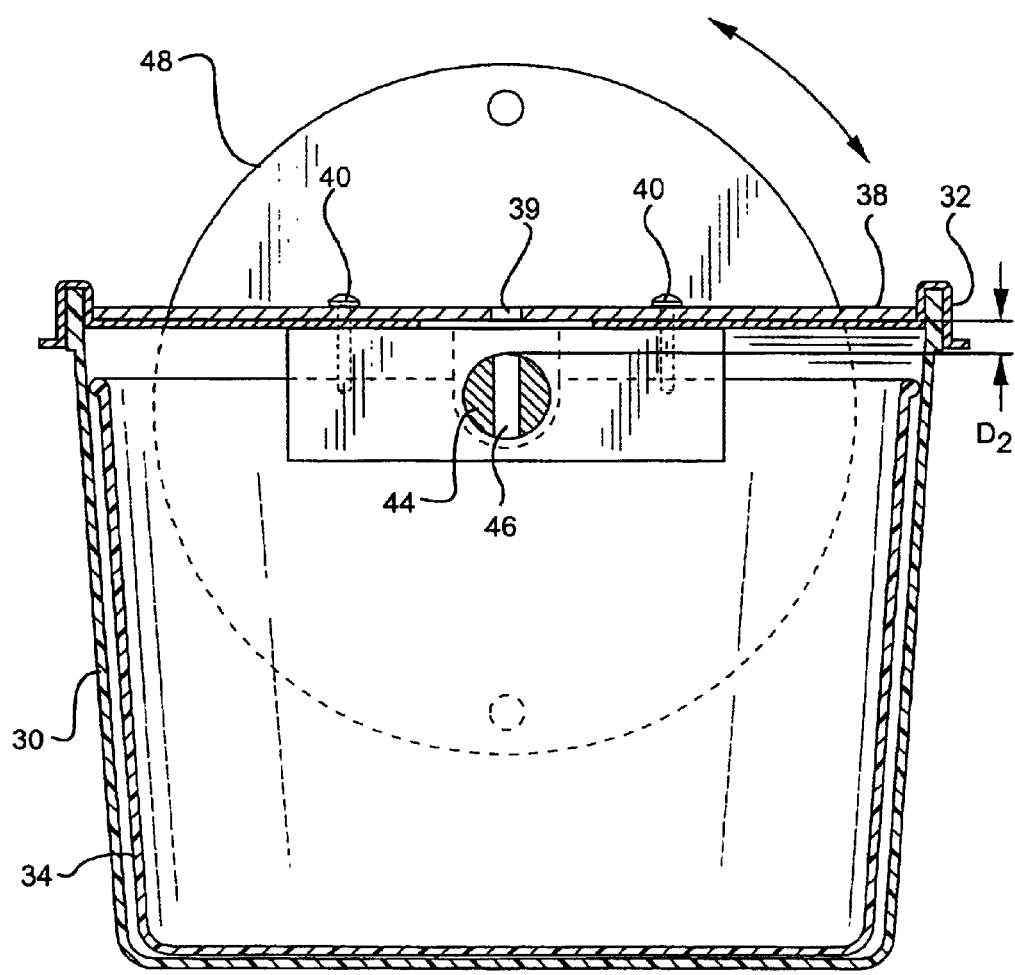
FIG. 3 is a side elevational view, in section, of the needle removal/destruction apparatus of FIG. 1.

Referring additionally to FIGS. 2–3, apparatus 10 includes a container 26 and a needle removing fixture 28. Container 26 includes a base 30 and a container top 32. Container top 32 can be removably secured to base 30 to allow emptying of apparatus 10 for subsequent reuse, or can be permanently secured to base 30 such that apparatus 10 is simply discarded once it is full. A collection receptacle 34 slides within base 30 for collection of used/destroyed needles, thus allowing ready removal of the used needles during emptying/sterilizing of apparatus 10 (assuming container top 32 is configured for removal from base 30).

As shown, needle removing fixture 28 is supported by bearing blocks 36a, 36b, which in turn are supported by a mounting plate 38. Mounting plate 38 includes an aperture 39 sized to allow needle 20 to pass therethrough until needle hub 22 contacts the mounting plate. A plurality of screws 40 extend through apertures formed in container top 32 and are threadably received by blocks 36a, 36b.

Needle removing fixture 28 includes a shaft 42 whose ends are received within and are rotatably supported by bearing blocks 36a, 36b. Needle removing fixture 28 further includes a working section 44 having a diameter greater than the diameter of shaft 42. A passage 46 extends through working section 44 and defines an axis L. A handle 48 is secured to one end of shaft 42, preferably in a press-fit fashion. To prevent loosening of handle 48 with respect to shaft 42, handle 48 includes a groove 50 which receives the ends of a pin 52 extending through shaft 42. It will be appreciated that the torque created by handle 48 is in part transmitted to shaft 42 via pin 52. To allow shaft 42 to extend outside of the container, base 30 is formed with a U-shaped notch 54 and collection receptacle 34 is formed with a U-shaped notch 56. Of course, apparatus 10 could incorporate structure other than handle 48 to accomplish the rotation of needle removing structure 28. Many known structures such as springs, linkages, gear assemblies, electric motors, hydraulic and pneumatic components and combinations thereof can be used to accomplish such rotation.

Figure 4:
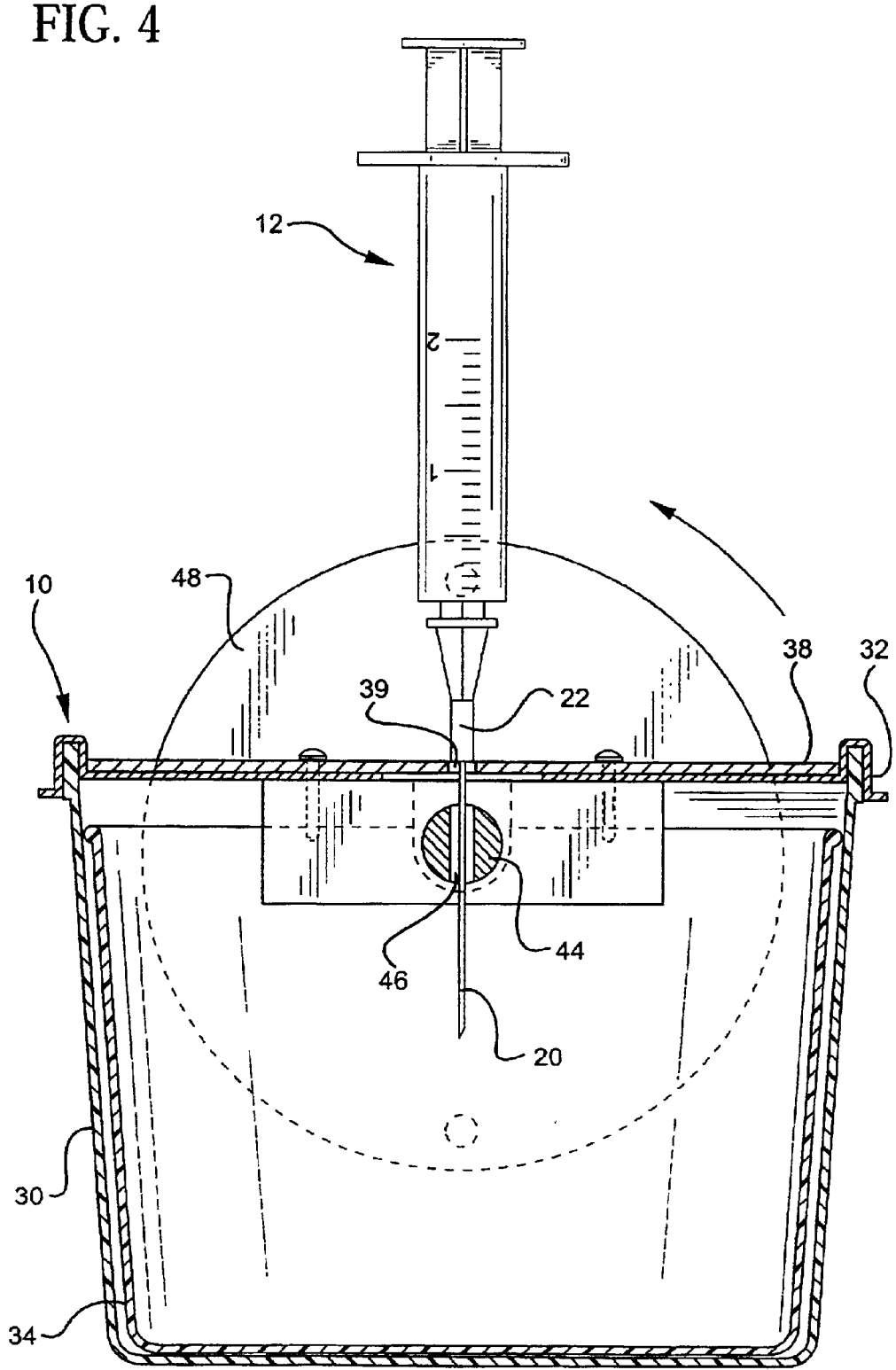
FIG. 4 is a view similar to FIG. 3 showing a hypodermic syringe engaging the needle removal/destruction apparatus and having its needle positioned for removal/destruction.
Figure 5:
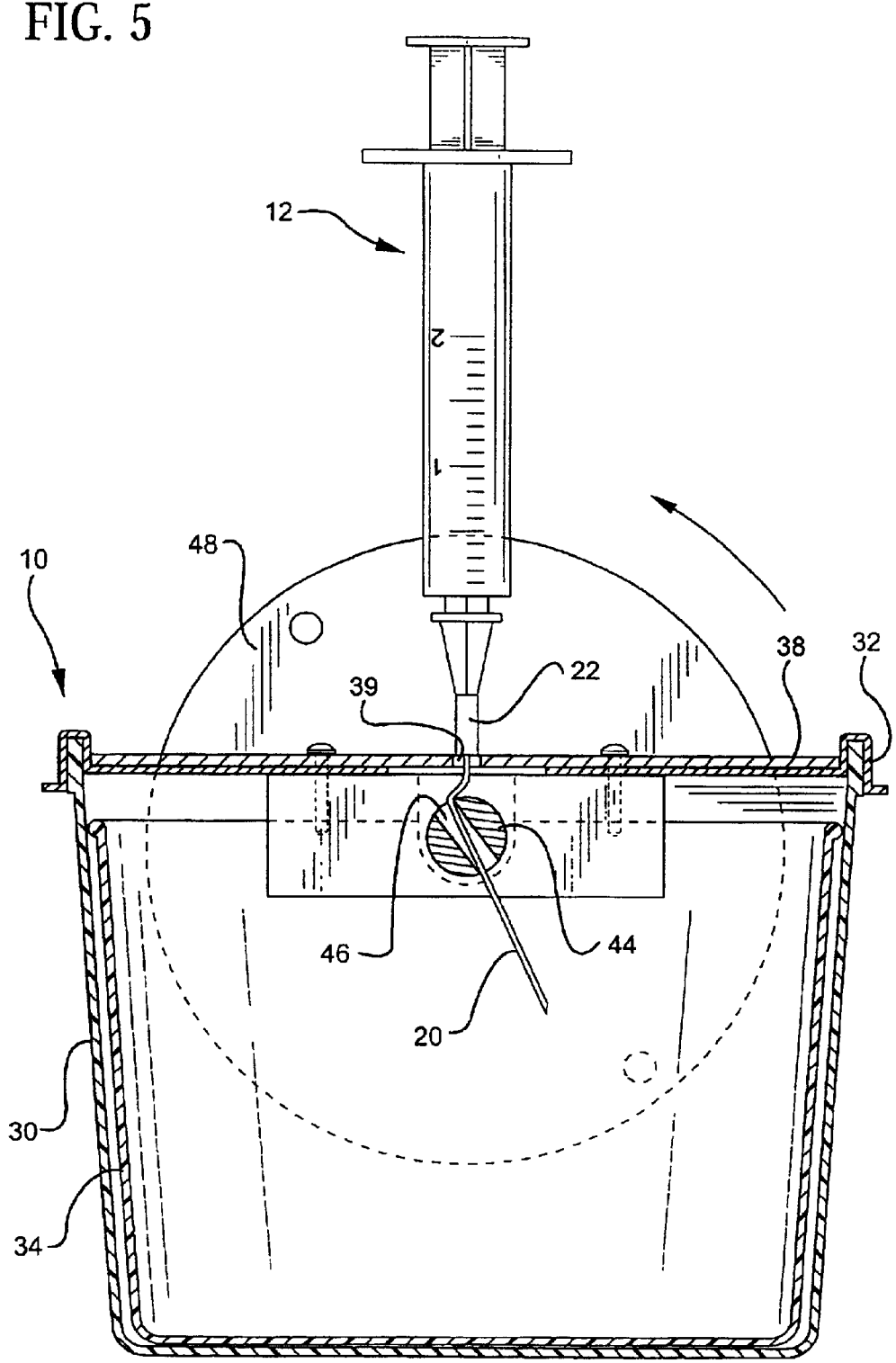
FIG. 5 is a view similar to FIG. 4 showing the needle removing fixture having been rotated approximately 45 counterclockwise thus initiating removal/destruction of the needle.
Figure 6:
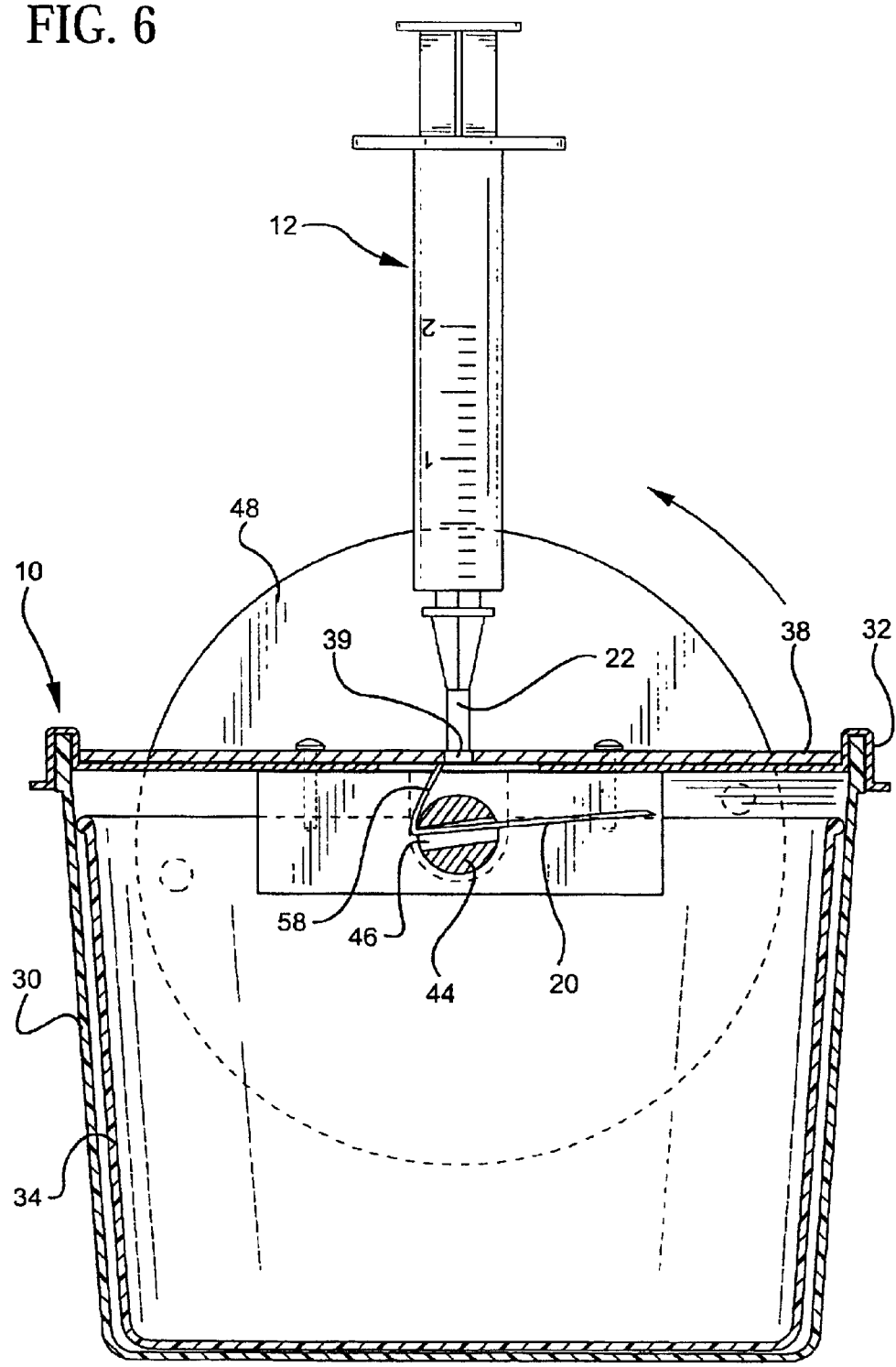
FIG. 6 is a view similar to FIG. 4 showing the needle removing fixture having been rotated approximately 90 counterclockwise wherein the needle has been entirely removed from the needle hub and wherein the end portion thereof is subjected to a bending stress.
Figure 7:
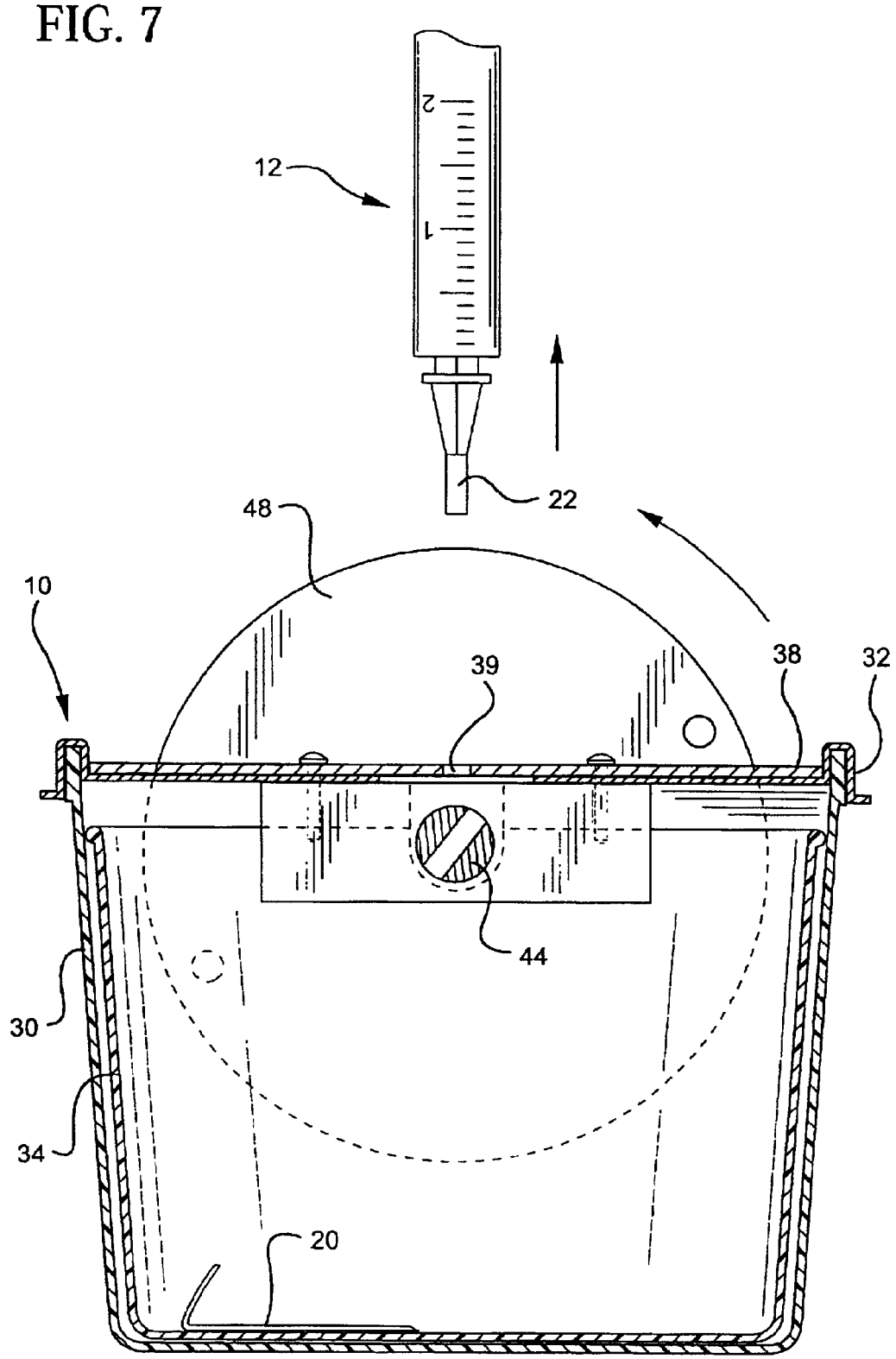
FIG. 7 is a view similar to FIG. 4 showing the removed/destroyed needle contained within the collection receptacle after having been ejected from the needle removing fixture.

The operation of apparatus 10 will now be described with reference to FIGS. 4–7. In this regard, FIG. 4 shows hypodermic syringe 12 engaging apparatus 10 wherein needle 20 extends though aperture 39 and is captured within passage 46 of needle removing fixture 28. As shown, aperture 39 formed in mounting plate 38 is sized to prevent needle hub 22 from passing therethrough. As handle 48 is rotated counterclockwise (see FIG. 5 showing needle removing fixture being rotated approximately 45° counterclockwise), needle 22 is at least partially deformed in the region proximate needle hub 22. At the same time, the rotation of the needle removing fixture exerts a force on needle 22 tending to pull needle 20 out of needle hub 22. Continued rotation of the needle removing fixture results in the needle being completely pulled out of the needle hub (see FIG. 6 showing needle removing fixture 28 being rotated approximately 90° counterclockwise). As a result, needle hub 22 is free of any metal fragments which could otherwise injure a handler of the used syringe. Moreover, there are no sharpened edges created on the syringe itself, nor are there any metal portions left in the syringe which could hinder subsequent disposal/recycling of the used syringe. As shown, continued rotation of the needle removing fixture results in the used/deformed needle being ejected from the needle removing fixture and captured within collection receptacle 34. (See FIG. 7).

Referring again to FIG. 6, working section 44 is preferably sized and located such that the end extent of the needle extending from passage 46 (i.e., end extent 58) is temporarily captured between passage 46 and the bottom of plate 38 as the needle removing fixture is rotated. This introduces a bending stress into this portion of the needle. It will be appreciated that continued rotating of the needle removing fixture will eventually release the end extent of the needle captured between the passage and the bottom of the plate, which causes the needle to be propelled out of the passage and ejected into the collection receptacle. The point at which this ejection of the needle occurs depends upon several factors including the diameter and location of working section 44, the size and length of the needle and the manner in which the needle is attached to the syringe.

Particularly, ejection of the needle from the needle removing fixture should occur at an orientation of greater than 90° and less than 180° to ensure the destroyed needle is directed into the collection receptacle and to minimize any risk of a destroyed needle becoming caught within the needle removing fixture. With this in mind and referring again to FIG. 6, the diameter of the working section is calculated such that the needle is preferably pulled free of the needle hub at an orientation of approximately 90°. The end of the needle pulled free from the hub is then stressed between passage 46 and the bottom of top plate 38 until the needle removing fixture is further rotated to an orientation which releases the stress introduced into the needle, thus allowing the needle to be ejected from the needle removing fixture into the collection receptacle.

Working section 44 is preferably located a distance $D_2$ from mounting plate 38, $D_2$ being great enough to ensure that the rotating needle removing fixture imparts a pulling force to the needle of the syringe, rather than shearing the needle from the syringe. In one preferred embodiment, distance $D_2$ encompasses a range of from about 0.5 mm to about 7 mm.

In addition to being spaced a distance $D_2$ from mounting plate 38, the space surrounding the outer circumference of working section 44 is also preferably free of shearing surfaces, that is, it is clear of any fixed structure which would create a shearing surface with respect to working section 44 as needle removing fixture 28 is rotated. The lack of any such fixed structure thus prevents shearing of the needle as the needle removing fixture is rotated, and ensures that the needle can be smoothly pulled free of the needle hub (without interference) and subsequently ejected therefrom.

The diameter of working section 44 determines the range of needle lengths that can be destroyed by the apparatus. Generally, a needle removing fixture having a working section with a smaller diameter can be used for shorter needles, while a needle removing fixture having a working section with a larger diameter can be used with longer needles.

In a preferred embodiment, working section 44 has a diameter of approximately 14 mm and is spaced from top plate 38 a distance of approximately 7 mm. This arrangement allows apparatus 10 to be used to destroy needles having a length from about 19 mm to about 60 mm, and a glue well length up to about 10 mm (which includes the vast majority of needles). To destroy needles having a length less than 19 mm (used in connection with certain specialty syringes), a second shaft can be added to the apparatus, this second shaft being located parallel to the first shaft and preferably driven by a gear drive cooperating with the first shaft. The size and location of the second shaft is calculated to destroy the mentioned shortened needles. Of course, a second aperture must then be included in plate 38.

Although apparatus 10 discussed hereinabove utilizes a rotatable needle removing fixture, other structure for pulling a needle out of the hub of a hypodermic syringe while simultaneously deforming such needle is contemplated herein. This alternative structure could include linearly or angularly movable grasping mechanisms which engage the needle within the container and pull the needle out of the needle hub without shearing, while also deforming the needle to prevent reuse. For example, the needle removing fixture described hereinabove could be replaced with structure which grasps the sharpened end of the needle and moves in a direction perpendicular to such needle, the needle being supported at its midsection by suitable structure (such as a cylinder) which allows deformation of the sharpened end of the needle thereabout while ensuring that the force imparted to the sharpened end of the needle results in the pulling of the needle free from the needle hub (without shearing).

Figure 8:
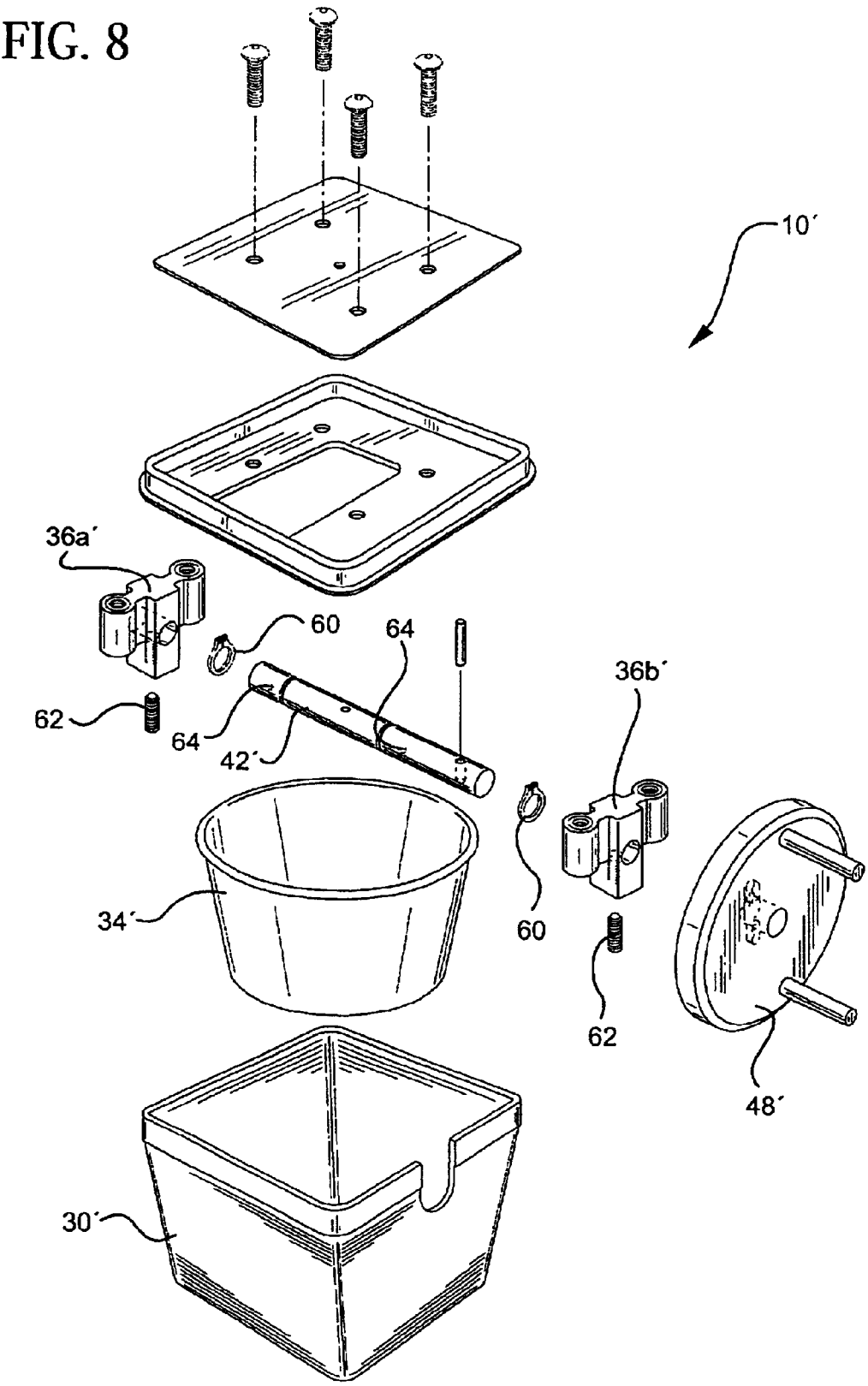
FIG. 8 is an exploded perspective view of an alternative needle removal/destruction apparatus.
Figure 9:
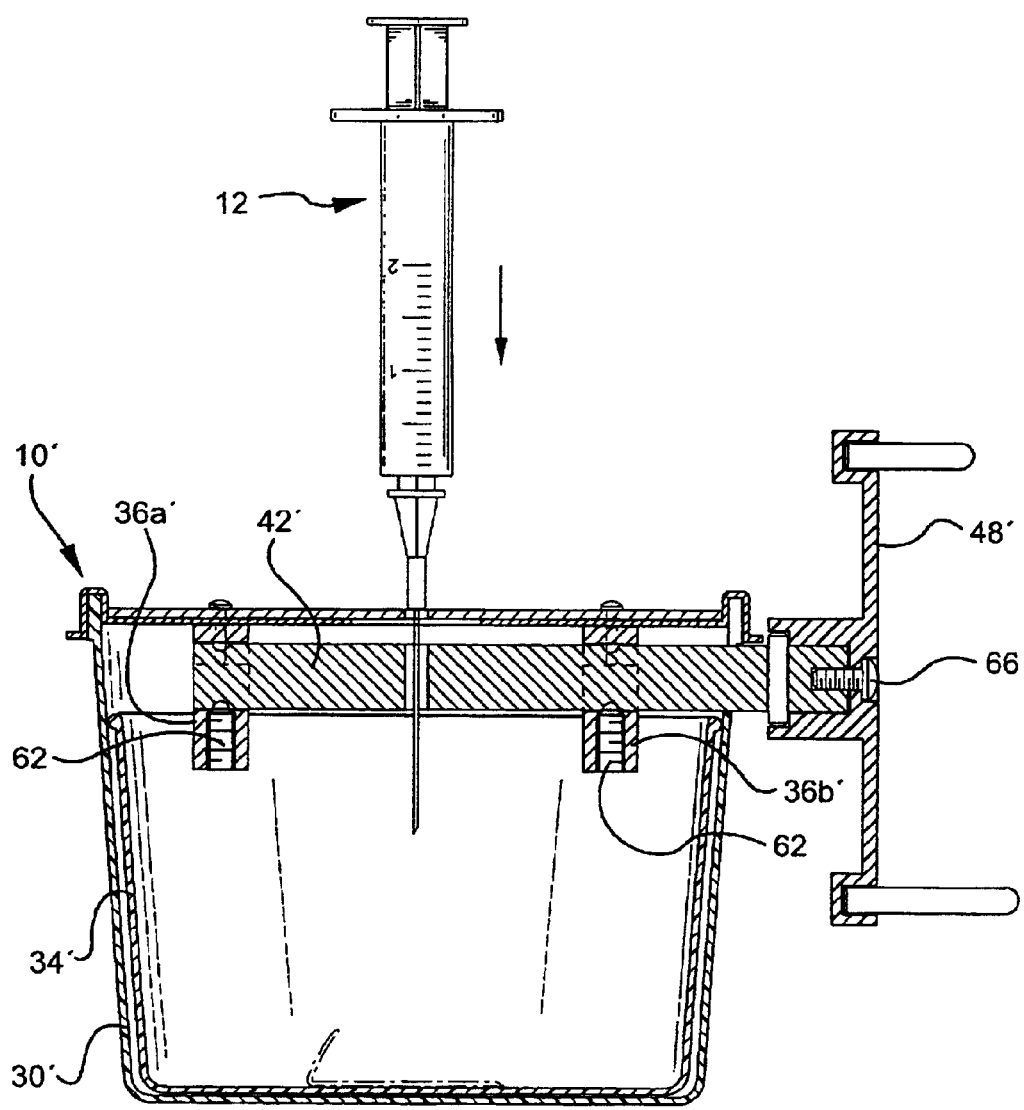
FIG. 9 is a side elevational view, in section, of the needle removal/destruction apparatus of FIG. 8.

FIGS. 8–9 illustrate an alternative embodiment of the present invention, i.e., needle removal/destruction apparatus 10', which includes a stepless shaft 42' of constant diameter. Shaft 42' is supported by bearing blocks 36a', 36b', and is held in position with respect to the bearing blocks by retaining rings 60. At least one of the bearing blocks includes a spring-loaded ball 62 which engages a detent 64 in the shaft when the shaft is oriented to align passage 46 with aperture 39. In this fashion, the medical personal using apparatus 10 can easily align passage 46 with aperture 39 so that insertion of needle 20 within passage 40 of the needle removing fixture can be readily accomplished. Handle 48' is preferably attached to shaft 42' via a screw 66. Finally, receptacle 34' is sized to fit within base 30' without the need of forming a U-shaped notch therein.

FIGS. 10–20 illustrate still another alternative embodiment of the present invention, i.e., needle removal/destruction apparatus 100. Apparatus 100 includes a container, i.e., collection box 102, preferably of a compact size whereby the apparatus can be conveniently transported, e.g., in a physician's pocket. The box, which can be as small as the size of a cigarette pack, can hold approximately 200 needles of assorted sizes.

Apparatus 100 also includes a needle removing fixture 104, which is rotatably supported by box 102 and secured thereto by a pair of retaining rings 164, 166 (which are similar in design to rings 60), the rings engaging grooves 106, 108. Needle removing fixture 104 includes a multiple-diameter shaft 110 having a first working section 112 of diameter $G_1$, and a second working section 114 of diameter $G_2$, $G_1$ being greater than $G_2$. A first passage 116 extends through first working section 112, while a second passage 118 extends through the second working section 114.

Figure 10:
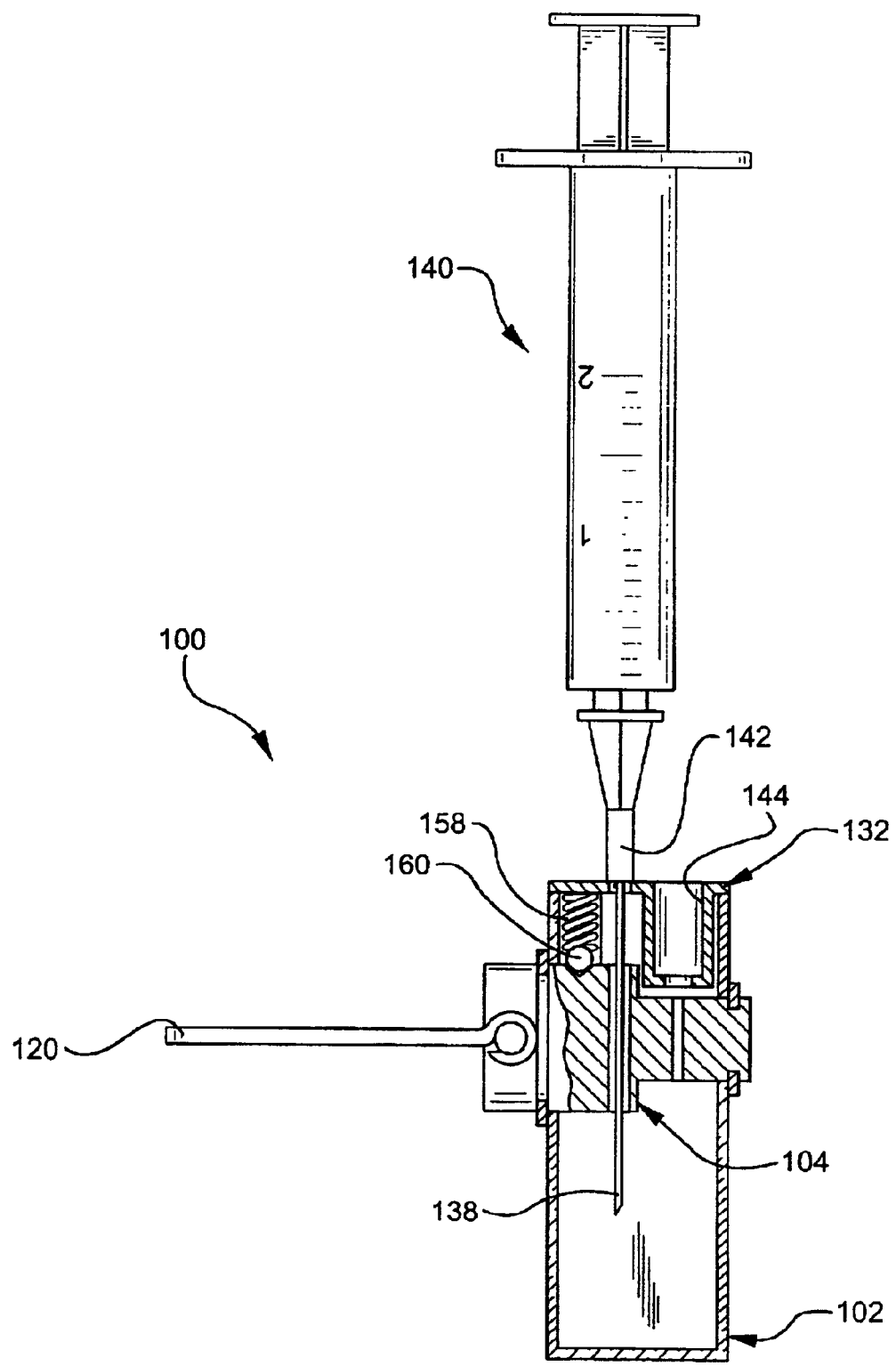
FIG. 10 is a side elevational view, in section, of another alternative needle removal/destruction apparatus showing a hypodermic syringe in engagement therewith.
Figure 11:
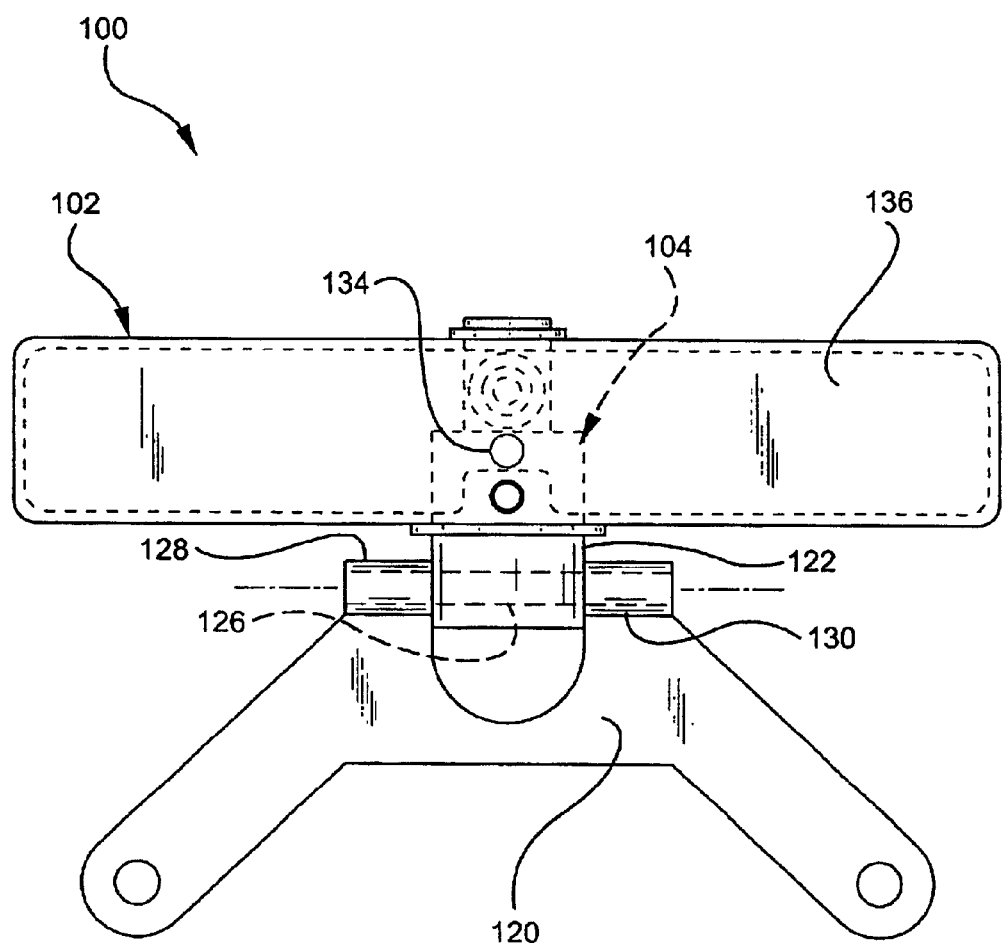
FIG. 11 is a top plan view of the apparatus of FIG. 10 with the hypodermic syringe removed therefrom.
Figure 12:
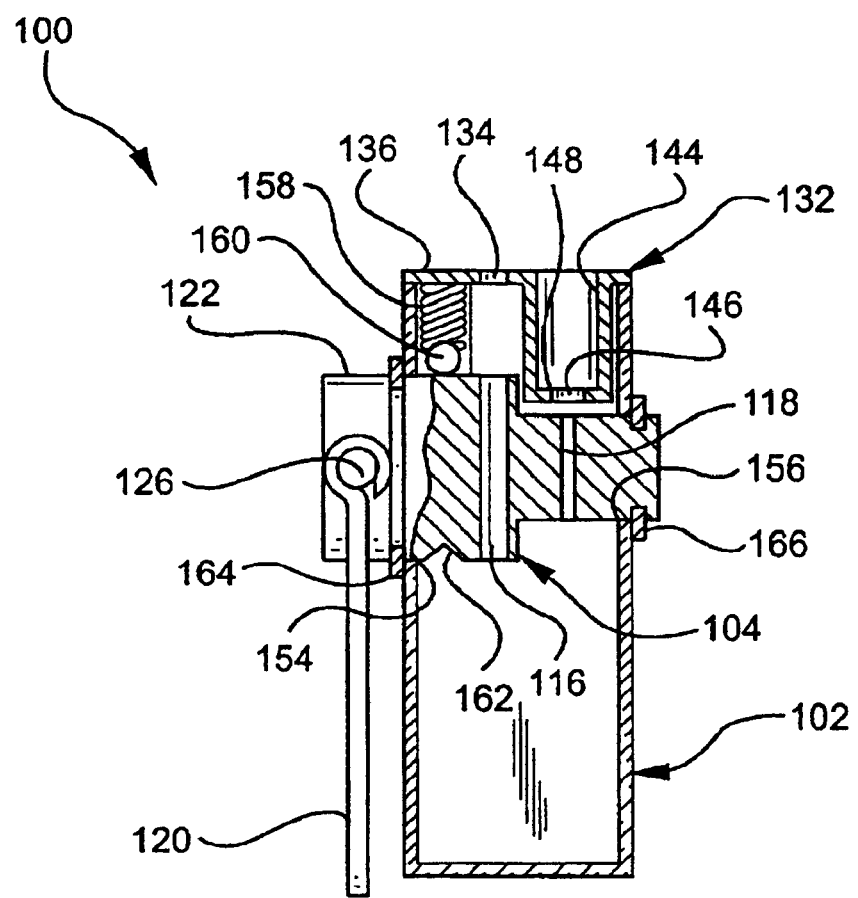
FIG. 12 is a side elevational view, in section, of the apparatus of FIG. 10 showing the key in its stowage position.
Figure 13:
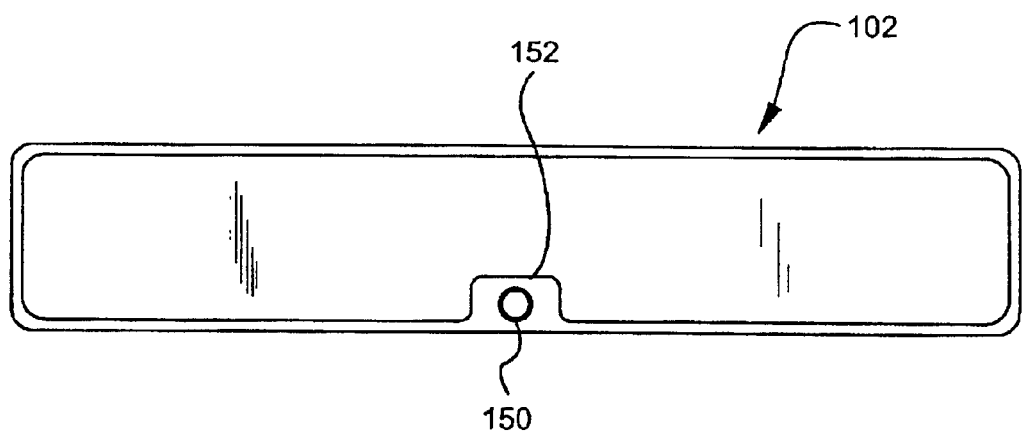
FIG. 13 is a top plan view of the container of the apparatus of FIG. 10.

As best shown in FIGS. 10, 11 and 12, a pivotable key 120 (which forms the operating handle in this embodiment) engages end 122 of the needle removing fixture. Particularly, end 122 protrudes out of box 102 and includes a bore 124 extending therethrough (see FIG. 17). A pin 126 is inserted through rings 128, 130 and bore 124, thereby pivotably securing key 120 to end 122 of the needle removing fixture. The key can be pivoted to a first operating position which is generally perpendicular to passages 116, 118 (see FIGS. 10 and 11), and can subsequently be pivoted to a second stowage position which is generally parallel to passages 116, 118 (see FIG. 12).

Container top 132, which is preferably ultrasonically welded to the box, includes a first aperture 134. As shown, aperture 134 is located along surface 136 of the container top. Accordingly, when needle 138 of syringe 140 is guided through aperture 134, the needle can be inserted until hub 142 contacts surface 136. As shown in FIG. 10, needle 138 extends through passage 116 of the needle removing fixture, whereby rotation of the needle removing fixture via key 120 will pull the needle free from the hub without shearing the needle, while simultaneously deforming the needle to prevent subsequent reuse.

Working section 112 (see FIG. 17), which includes passage 116, is preferably sized and located to be capable of pulling needles having a length equal to or greater than about 12 mm. Working section 114, which includes passage 118, is preferably sized and located to be capable of pulling needle having a length less than or equal to about 12 mm. In this regard, container top 132 includes a recessed sleeve 144 having an aperture 146 located therein. Sleeve 144 is sized to allow needle hub 142 to fit therein whereby needle 138 can be inserted through aperture 146 and into passage 118 of the needle removing fixture. The needle is inserted until hub 142 contacts surface 148 of sleeve 144.

As a result, the distance between surface 148 and working section 114 is less than the distance between surface 136 and working section 112. This reduced distance, together with the reduced diameter of working section 114, allows this second working section of the needle removing fixture to be capable of destroying needles having a length of less than or equal to about 12 mm.

Figure 15:
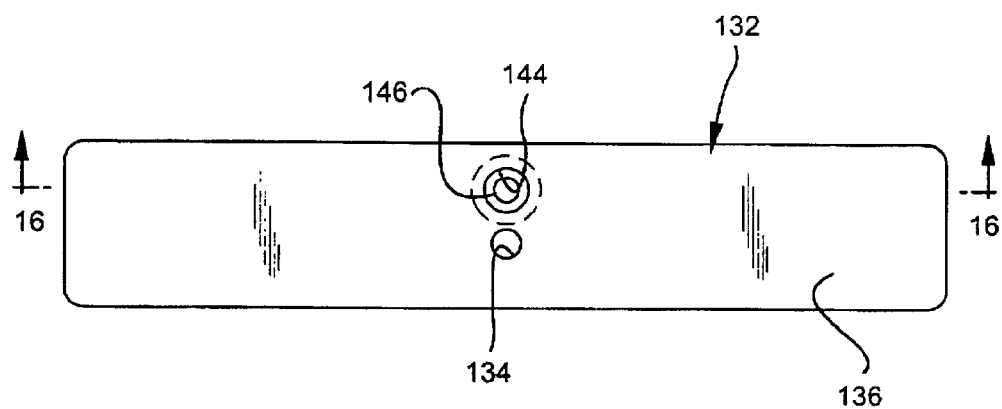
FIG. 15 is a top plan view of the container top of the apparatus of FIG. 10.
Figure 16:
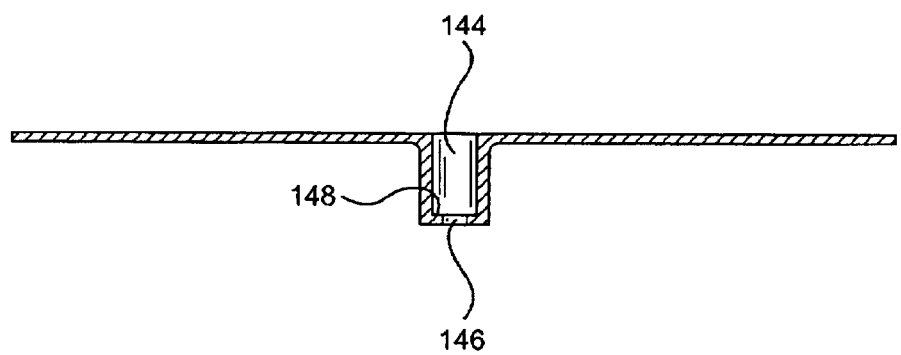
FIG. 16 is a sectional view taken along lines 16-16 of FIG. 15.
Figure 17:
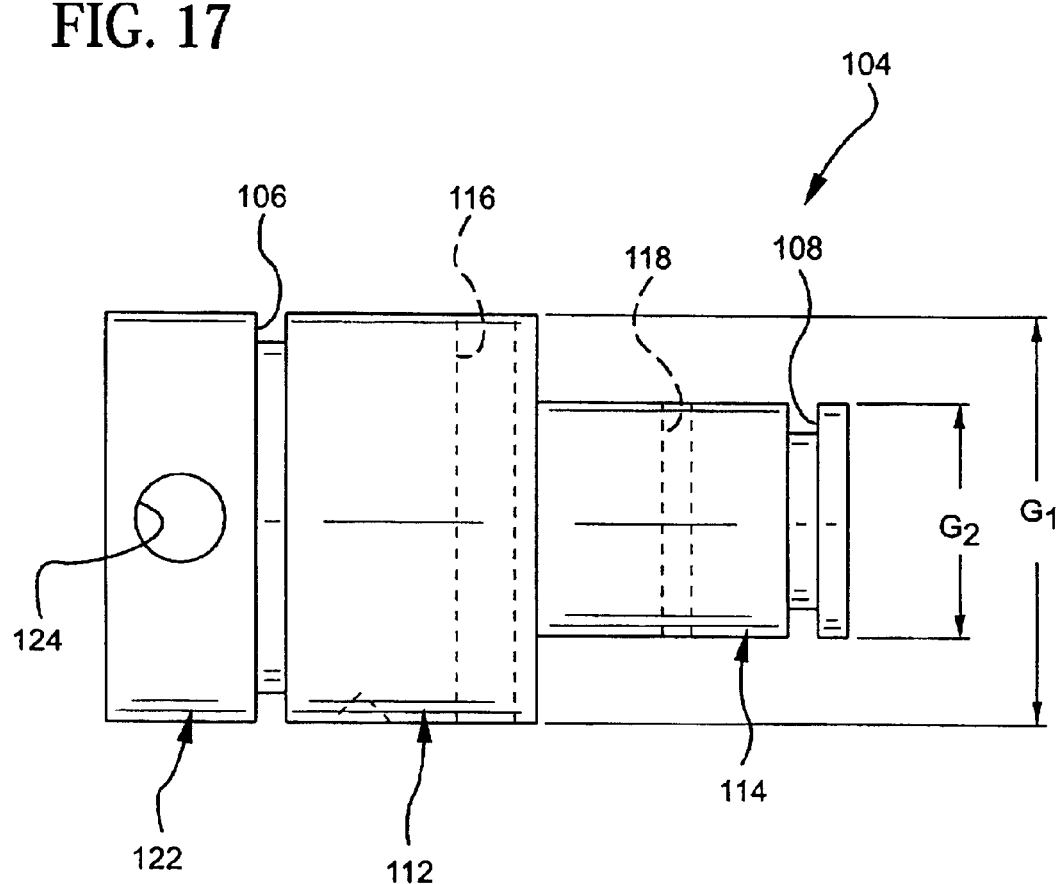
FIG. 17 is an enlarged detail of the needle removing fixture of the apparatus of FIG. 10.
Figure 18:
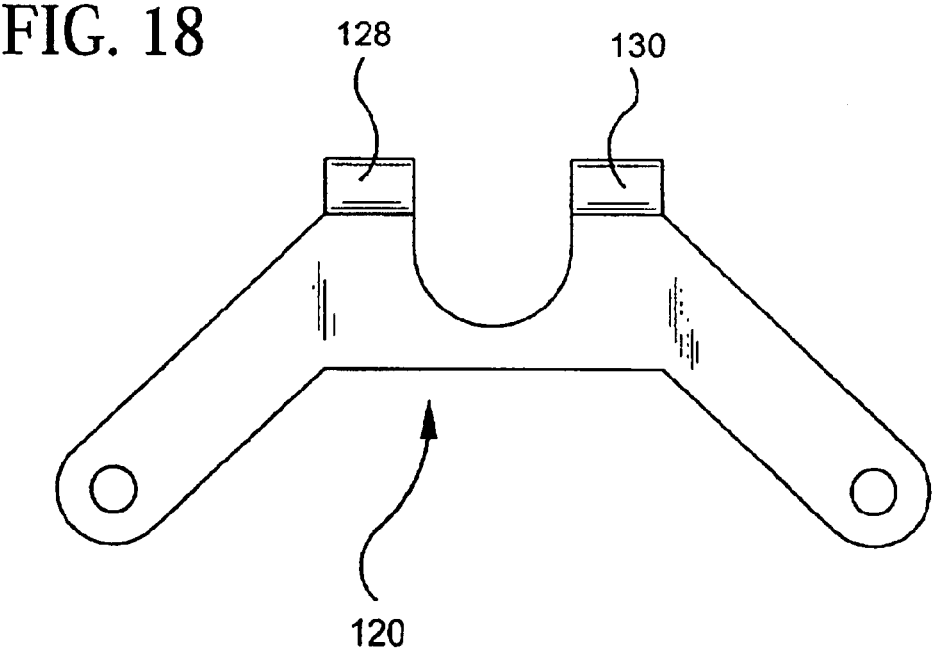
FIG. 18 is a front elevational view of the key of the apparatus of FIG. 10.
Figure 19:
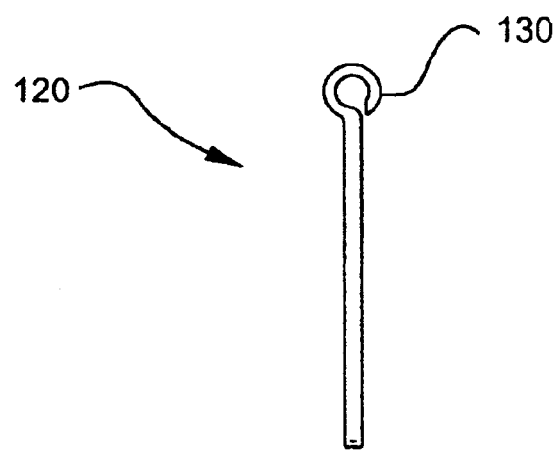
FIG. 19 is a side elevational view of the key of FIG. 19.

Recessed sleeve 144 can be circular in cross-section (as shown in FIGS. 15–16) or, alternatively can be formed with a rectangular cross-section. In one such alternative embodiment, the recessed sleeve is formed from a U-shaped bracket attached to the inside surface of the container top.

Figure 14:
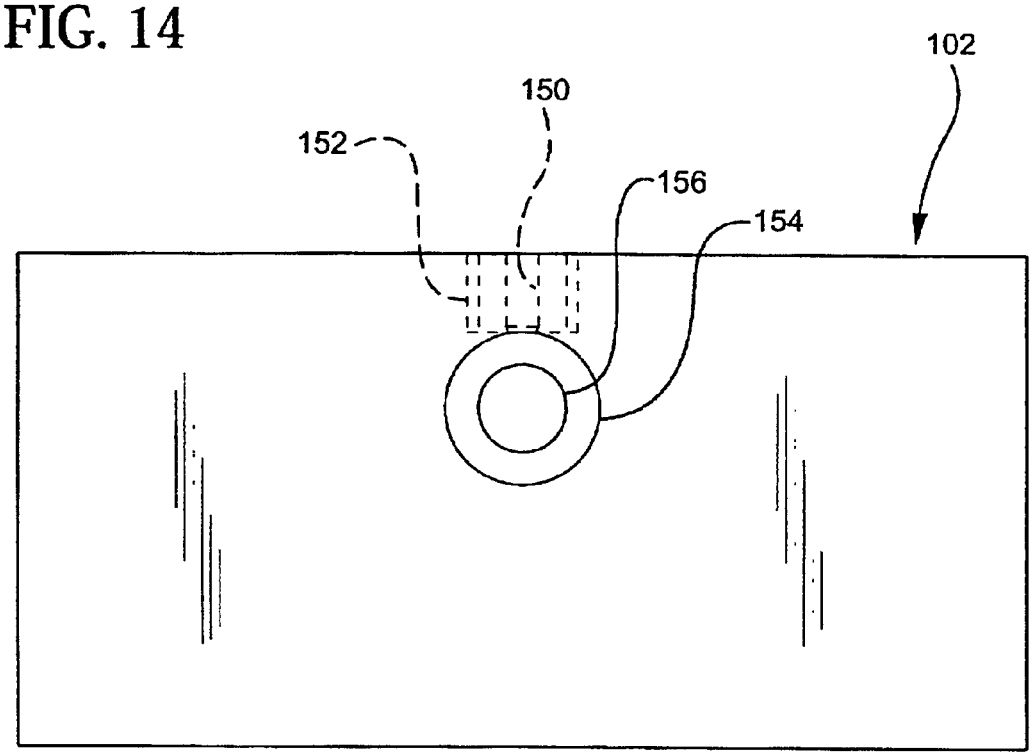
FIG. 14 is a front elevational view of the container of FIG. 14.

Box 102 preferably includes a circular channel 150 for receipt of a spring-loaded ball detent including a spring 158 and a ball 160. The spring-loaded ball engages a notch 162 formed on the needle removing fixture so as to facilitate the aligning of passages 116, 118 with apertures 134, 146, respectively. Circular channel 150 is formed within a block 152, which is integrally molded with the box. As best shown in FIG. 14, box 102 includes apertures 154, 156 sized to allow the needle removing fixture to extend therethrough.

In one alternative embodiment, box 102 is formed from a plastic material which is preferably transparent to allow viewing of the interior of the box. The walls of the box are formed with a thickness sufficient to allow channel 150 to be formed directly therein.

Apparatus 100 operates in the same manner as apparatus 10 discussed hereinabove, that is, the needle is pulled from the hub of the syringe without shearing of the needle. The needle is permanently deformed during this removal process, and is subsequently ejected into the collection box. Once the box is full, the entire apparatus can be discarded. Alternatively, the needle removing fixture can be removed and installed on an empty box.

It will be appreciated that the present invention has been described herein with reference to certain preferred or exemplary embodiments. The preferred or exemplary embodiments described herein may be modified, changed, added to or deviated from without departing from the intent, spirit and scope of the present invention, and it is intended that all such additions, modifications, amendments and/or deviations be included within the scope of the following claims.

What is claimed is:

1. An apparatus for removing a needle from a medical device, comprising:
   a container defining a chamber, said container including a container top having an aperture communicating with said chamber;
   a needle removing fixture rotatably mounted to said container top and rotatable with respect thereto free of shearing surfaces, said needle removing fixture being positioned at least partially within said chamber and including a passage for receiving a needle extending through said aperture in said container top; and
   a handle coupled to said needle removing fixture for rotating said needle removing fixture.

2. The apparatus as described in claim 1, wherein said passage includes an axis that is substantially alignable with said aperture in said container top.

3. The apparatus as described in claim 2, wherein said passage extends entirely through said needle removing fixture.

4. The apparatus as described in claim 1, wherein said handle extends at least partially outside said container.

5. The apparatus as described in claim 1, wherein said needle removing fixture includes a shaft having a working section located thereon, said passage being formed in said working section of said shaft; and
   further comprising a pair of bearing blocks for rotatably supporting the opposing ends of said shaft, each of said bearing blocks being mounted to said container top.

6. The apparatus as described in claim 5, further comprising a mounting plate, said mounting plate cooperating with said container top to mount said bearing blocks thereto, said opening being formed in said mounting plate.

7. The apparatus as described in claim 1, wherein said container includes a base, said container top being removably mounted to said base.

8. The apparatus as described in claim 7, further comprising a collection receptacle positioned within said container for collecting the needle removed from the medical device.

9. The apparatus as described in claim 1, wherein said passage includes an axis, said needle removing fixture being rotationally positionable such that said axis of said passage is substantially perpendicular to said container top.

10. A method of removing a needle from a medical device, comprising:

inserting said needle of said medical device into a passage of a needle removing fixture, wherein said needle removing fixture is rotatably mounted to a top of a container, and rotating said needle removing fixture about an axis via a handle while maintaining said medical device in a substantially stationary position, thereby removing said needle from said medical device without shearing thereof.

11. The method as described in claim 10, including rotating said needle removing fixture about an axis running substantially perpendicular to a longitudinal axis of said passage.

12. The method as described in claim 10, further including capturing said needle in a container once removed from said medical device.

13. The method as described in claim 12, including passing said needle through an aperture in said top of said container prior to inserting said needle into said passage.

14. The method as described in claim 13, including causing said medical device to engage said container top.

15. The method as described in claim 13, including aligning said passage and said aperture prior to inserting said needle into said passage.

16. A method of removing a metal needle from a plastic hub of a medical device, comprising:

securing said medical device in a substantially stationary position whereby said needle is located at a predetermined position;

disconnecting said metal needle from said plastic hub without shearing of said needle by rotating said needle in a needle removal fixture that is rotatably mounted to a container, wherein said needle is deformed to prevent reuse thereof.

17. The method as described in claim 16, further including capturing said needle in a container once removed from said medical device.

18. The method as described in claim 17, including passing said needle through an aperture in a top of said container prior to inserting said needle into a passage.

19. The method as described in claim 18, including causing said medical device to engage said container top.

* * * * *